United States Patent [19]

Shapiro

[11] E Patent Number: Re. 32,112

[45] Reissued Date of Patent: Apr. 15, 1986

[54] SPIRONOLACTONE-CONTAINING COMPOSITION AND USE THEREOF

[76] Inventor: German Shapiro, 938 Eudora St., Denver, Colo. 80220

[21] Appl. No.: 596,290

[22] Filed: Apr. 3, 1984

Related U.S. Patent Documents

Reissue of:

[64] Patent No.: 4,347,245
Issued: Aug. 31, 1982
Appl. No.: 266,924
Filed: May 26, 1981

[51] Int. Cl.[4] ..... A61K 31/58
[52] U.S. Cl. ..... 514/172
[58] Field of Search ..... 424/241, 238; 514/172

[56] References Cited

U.S. PATENT DOCUMENTS 3,257,390 6/1966 Patchett ..... 424/241

OTHER PUBLICATIONS

Shapiro et al., "Journal of Clinical Endocrinology and Metabolism, 51; p. 429 (1980).
Boisselle et al., "Fertility and Sterility; vol. 32, No. 3, Sep. 1979, pp. 276-279.
Ober et al., "Annals of Internal Medicine" 89 No. 5 (Part 1) Nov. 1978, pp. 543-544.
Chem. Abst. 83(21) 172,881t, An Abstract of the Publication in "Endocrinology", 97(1) pp. 52-58.

*Primary Examiner*—Elbert L. Roberts
*Attorney, Agent, or Firm*—Wegner & Bretschneider

[57] ABSTRACT

A composition containing spironolactone in an amount effective to suppress excess androgenic activity. The spironolactone-containing composition is applied directly to the skin site afflicted with excess androgens.

12 Claims, No Drawings

SPIRONOLACTONE-CONTAINING COMPOSITION AND USE THEREOF

Matter enclosed in heavy brackets [ ] appears in the original patent but forms no part of this reissue specification; matter printed in italics indicates the additions made by reissue.

BACKGROUND OF THE INVENTION

I. Technical Field

The present invention relates to a composition containing spironolactone, and more particularly, to such a composition containing spironolactone for application directly to human skin for effectively suppressing excess androgenic activity at the skin site.

II. Background Art

In most physically normal women, androgens or male sex homones are effectively synthesized by both ovaries and adrenals. However, in certain females afflicted with polycystic ovarian disease or ovarian hyperthecosis, the ovaries appear to be the major source of enhanced androgen secretion, especially testosterone. Such excess androgen secretion in women has been linked to increased masculine characteristics, in particular, hirsuitism.

A number of prior art compounds possessing antiandrogenic activity have been utilized in treatment of hirsuitism, as detailed in: A Novel Use of Spironolactone; Treatment of Hirsuitism, "Journal of Clinical Endocrinology and Metabolism" Shapiro, et al., Vol. 51, No. 3, pp. 429–432, Jan. 4, 1980; Spironolactone Therapy for Hirsuitism in a Hyper androgenic Woman, "Annals of Internal Medicine", Ober, et al., Vol. 89, No. 5 (Part 1), pp. 643, 644, November, 1978; and New Therapeutic Approach to the Hirsute Patient, "Fertility and Sterility", Boiselle, et al., Vol. 32, No. 3, pp. 276–279, September, 1979. Cyproterone acetate has been orally administered to treat hirsuitism and has proved effective therein. However, severe side effects, such as, adrenal insufficiency and loss of libido have rendered its use undesirable. Oral contraceptives and corticosteroids have also been utilized for treatment with androgenic access, although numerous side effects have minimized the use thereof. Spironolactone has also been orally administered for treatment of excess androgens in women. However, when spironolactone is administered orally, the concentration of spironolactone must be increased to a level at which equal concentrations are provided to all tissue even though specific skin tissue at which excess androgenic activity occurs may be the only desired area to be treated. If spironolactone is administered orally on a daily basis, side effects, such as, metrorrhagia (i.e., disruption of the menstrual cycle during which non-menstrual bleeding from the uterus occurs) and electrolytic disturbance involving potassium accumulation in the blood, may occur. Thus, oral ingestion of spironolactone must be constantly monitored by a licensed physician which is both costly and time consuming. In addition, as spironolactone should only be orally administered to women between the fifth and twenty second day of their menstrual cycle to aovid metrorrahgia, a woman must constantly be appraised of and cognizant of this fact. Finally, even when spironolatone is properly administered orally, large amounts of tissue which are not afflicted with an excess of androgenic activity are unnecessarily intoxicated with spironolactone.

Thus, it can be appreciated that a need exists for a composition possessing antiandrogenic activity which can be applied directly to human skin for effectively suppressing the excess androgenic activity thereof.

BRIEF SUMMARY OF THE INVENTION

The present invention relates to a spironolactone containing composition for effectively suppressing excess androgenic activity which occurs at a skin site to effectively treat, inter alia, hirsuitism. The composition consists essentially of an effective amount of spironolactone incorporated into a carrier. A solubilizer, a viscosifier and a preservative may also be selectively incorporated into the composition of the present invention as desired.

DETAILED DESCRIPTION

The present invention relates to a spironolactone-containing composition for application to an area of human skin afflicted with hirsuitism for effective treatment thereof. Applicant has discovered that by direct application of spironolactone to an afflicted area of human skin via a suitable carrier, hirsuitism in the afflicted area is effectively controlled and reduced while substantially eliminating any side effects attendant with use of spironolactone. It is believed that spironolactone suppresses androgenic activity in the skin which is a major site of androgene metabolism.

The composition of the present invention comprises an effective amount of spironolactone and a suitable [liquid] carrier. As utilized throughout the description, the term "spironolactone" refers to aldactone [3-(3-oxo-7-acethylthio-17-hydroxy-antrost-4-en-17-4yl) propionic acid lactone]. The [liquid] carrier can be any [liquid] carrier which can function to transport an active ingredient to the area of human skin to be treated and preferably which is capable of being rubbed into the skin so as to be transparent in appearance. Exemplary [liquid] carriers are alcohol, urea, mineral oil and white petrolatum. Depending upon the exact [liquid] carrier employed and the addition of any viscosifiers, the composition of the present invention can have characteristics ranging from those of a cream to an ointment.

In accordance with the preferred embodiment, spironolactone is incorporated into the composition of the present invention in the amount of from about 0.25 wt. % to about 2.0 wt. %, and most preferably about 1.0 wt. %. Spironolactone can be incorporated into a suitable carrier in a preselected amount as dictated by the concentration ranges just described.

A solubilizer, such as, stearyl alcohol, or cetyl alcohol, can be utilized in the composition of the present invention to solubilize spironolactone therein so as to aid incorporation of spironolactone into the carrier. The solubilizer can be incorporated into the composition of the present invention in an amount of from about 1.5 wt. % to about 3.0 wt. %. A viscosifier, such as, cottonseed oil, can also be incorporated into the composition of the present invention where a lower viscosity is desirable and/or to aid in emulsification of the solubilizer within the carrier. The viscosifier can be incorporated into the composition of the present invention in an amount of from about 3 wt. % to about 6 wt. %. A preservative, such as, methylhydroxybenzoate, propylhydroxybenzoate, or mixtures thereof, can also be incorporated into the composition of the present invention in an amount from about 0.25 wt. % to about 0.50 wt. %.

The preferred composition of the present invention is about 1.0 wt. % spironolactone, about 1.5 wt. % stearyl alcohol, about 3.0 wt. % cottonseed oil, about 0.25 wt. % methylhydroxybenzoate, and about 94.25 wt. % white petrolatum.

The composition of the present invention may be manually applied to the afflicted area of skin and rubbed until absorbed fully into the area. Concomitant with a reduction of hirsuitism in the area treated, is an improvement of acne which is also a disorder known to be androgen dependent. Thus, it can be appreciated that in utilizing the spironolactone-containing composition of the present invention, the entire physical system of an individual treated is not intoxicated with spironolactone but only that surface skin area to be treated, thus minimizing side effects attendant with application of spironolactone and constant physician monitoring which is attendent with oral ingestion of spironolactone. And although the composition of the present invention has been described as effective in treating hirsuitism in women, the composition is also effective in retarding baldness in men since such baldness is characterized by excess andgrogenic activity.

While various embodiments and modifications of the invention have been described in the foregoing description, further modifications will be apparent to those skilled in the art. Such modifications are included within the scope of this invention as defined by the following claims.

I claim:

1. A composition for effectively suppressing excess androgenic activity which occurs at a skin site so as to effectively treat [hirsuitisum] *hirsutism,* said composition being [directly applied] *in a form suitable for direct application* to said skin site [, the composition] *and* consisting essentially of [: a liquid carrier selected from the group consisting of alcohol, urea, mineral oil and white petrolatum; and ] spironolactone in an amount of from about 0.25 wt. % to about 5.0 wt. %, which effectively suppresses excess androgenic activity at said skin site, *in a suitable carrier therefor; said composition having characteristics ranging from those of a cream to those of an ointment.*

2. The composition of claim 1 wherein [said liquid] *the* carrier is white petrolatum.

3. The composition of claim 1 further consisting essentially of:

a solubilizer selected from the group consisting of stearyl alcohol, cetyl alcohol or mixtures thereof, said solubilizer being present in an amount of from about 1.5 wt. % to about 3.0 wt. % so as to aid incorporation of said spironolactone into said carrier.

4. The composition of claim 3 further consisting essentially of a viscosifier in an amount sufficient to aid in emulsification of said solubilizer in said carrier.

5. The composition of claim 1 further consisting essentially of:

a preservative selected from the group consisting of methylhydroxybenzoate, propylhyroxybenzoate, or mixtures thereof, said preservative being employed in an amount sufficient to extend the useful like of said composition.

6. In a process for treating at least one skin site characterized by excess androgenic activity so as to effectively suppress said excess androgenic activity, the improvement comprising: directly applying a spironolactone-containing composition to said at least one skin site, said composition consisting essentially of [a liquid carrier selected from the group consisting of alcohol, urea, mineral oil and white petroleum and] spironolactone in an amount of from about 0.25 wt. % to about 5.0 wt. % *in a suitable carrier therefor,* which effectively suppresses androgenic activity at said skin site.

7. The process of claim 6 wherein said [liquid] carier is white petrolatum.

8. The process of claim 6 wherein said composition further consists essentially of a solubilizer selected from the group consisting of stearyl alcohol, cetyl alcohol or mixtures thereof, said solubilizer being present in an amount of from about 1.5 wt. % to about 3.0 wt. % so as to aid incorporation of said spironolactone into said carrier.

9. The process of claim 8 wherein said composition further consists essentially of a viscosifier in an amount sufficient to aid in emulsification of said solubilizer in said carrier.

10. The process of claim 6 wherein said composition further consists essentially of a preservative selected from the group consisting of methylhydroxybenzoate, propylhydroxybenzoate, or mixtures thereof, said preservative being employed in an amount sufficient to extend the useful life of said composition.

*11. The process according to claim 6 for the treatment of hirsutism caused by excess androgenic activity.*

*12. The process according to claim 6 for the treatment of acne caused by excess androgenic activity.*

* * * * *